United States Patent [19]
Barbier

[11] Patent Number: 5,765,994
[45] Date of Patent: Jun. 16, 1998

[54] LOW OIL DETECTOR WITH AUTOMATIC RESET

[76] Inventor: William J. Barbier, 6720 Christina Marie La., Hazelwood, Mo. 63042

[21] Appl. No.: 502,632

[22] Filed: Jul. 14, 1995

[51] Int. Cl.⁶ .................................. F04B 49/00; F04B 49/10
[52] U.S. Cl. .................................. 417/12; 417/13; 73/293; 250/577; 62/129; 62/193
[58] Field of Search .................................. 417/12, 13, 36; 340/619, 514, 645; 250/577; 73/293; 62/126, 129, 193

[56] References Cited

U.S. PATENT DOCUMENTS

| | | | |
|---|---|---|---|
| 3,059,443 | 10/1962 | Garner | 62/126 |
| 4,134,022 | 1/1979 | Jacobsen | 250/577 |
| 4,155,013 | 5/1979 | Spiteri | 250/577 |
| 4,354,180 | 10/1982 | Harding | 340/619 |
| 4,383,802 | 5/1983 | Gianni et al. | 417/12 |
| 4,990,057 | 2/1991 | Rollins | 417/12 |
| 5,029,471 | 7/1991 | Goodrich | 73/293 |
| 5,072,595 | 12/1991 | Barbier | 62/129 |
| 5,088,324 | 2/1992 | Nemeth | 250/577 |
| 5,103,648 | 4/1992 | Barbier | 62/126 |
| 5,257,539 | 11/1993 | Gale et al. | 73/293 |

FOREIGN PATENT DOCUMENTS

| | | | |
|---|---|---|---|
| 405172074 | 7/1993 | Japan | 417/13 |
| 406033889 | 2/1994 | Japan | 417/13 |

*Primary Examiner*—Timothy Thorpe
*Assistant Examiner*—Xuan M. Thai
*Attorney, Agent, or Firm*—Daniel E. Kramer

[57] ABSTRACT

An optical liquid level sensor for distinguishing between the presence of oil and vapor within a compressor crankcase. The sensor has a light transmitting window positioned to interface the crankcase interior and a planar side facing the crankcase exterior. A light source and a light sensor are both positioned adjacent the exterior face of the window. The sensor has a first condition when the prismatic face is immersed in oil and a second condition when the prismatic face is immersed in vapor. An electronic circuit having a dual MOSFET switch for alternating current is mounted adjacent the light source and sensor. The circuit provides power to the source and monitors the sensor. When the sensor is in the first condition, the circuit closes the switch. When the sensor detects the second condition, the circuit starts a timer and continuously tests the condition of the sensor. If the first condition is detected, the timer resets to its initial value. If the second condition continues for the full time period, the circuit opens the switch. On the opening of the switch, the circuit continuously tests for the condition of the sensor. If the sensor returns to the first condition, the circuit closes the switch. An external switch is provided to manually reset the timer to its initial value and cause the switch to close for the time period.

10 Claims, 4 Drawing Sheets

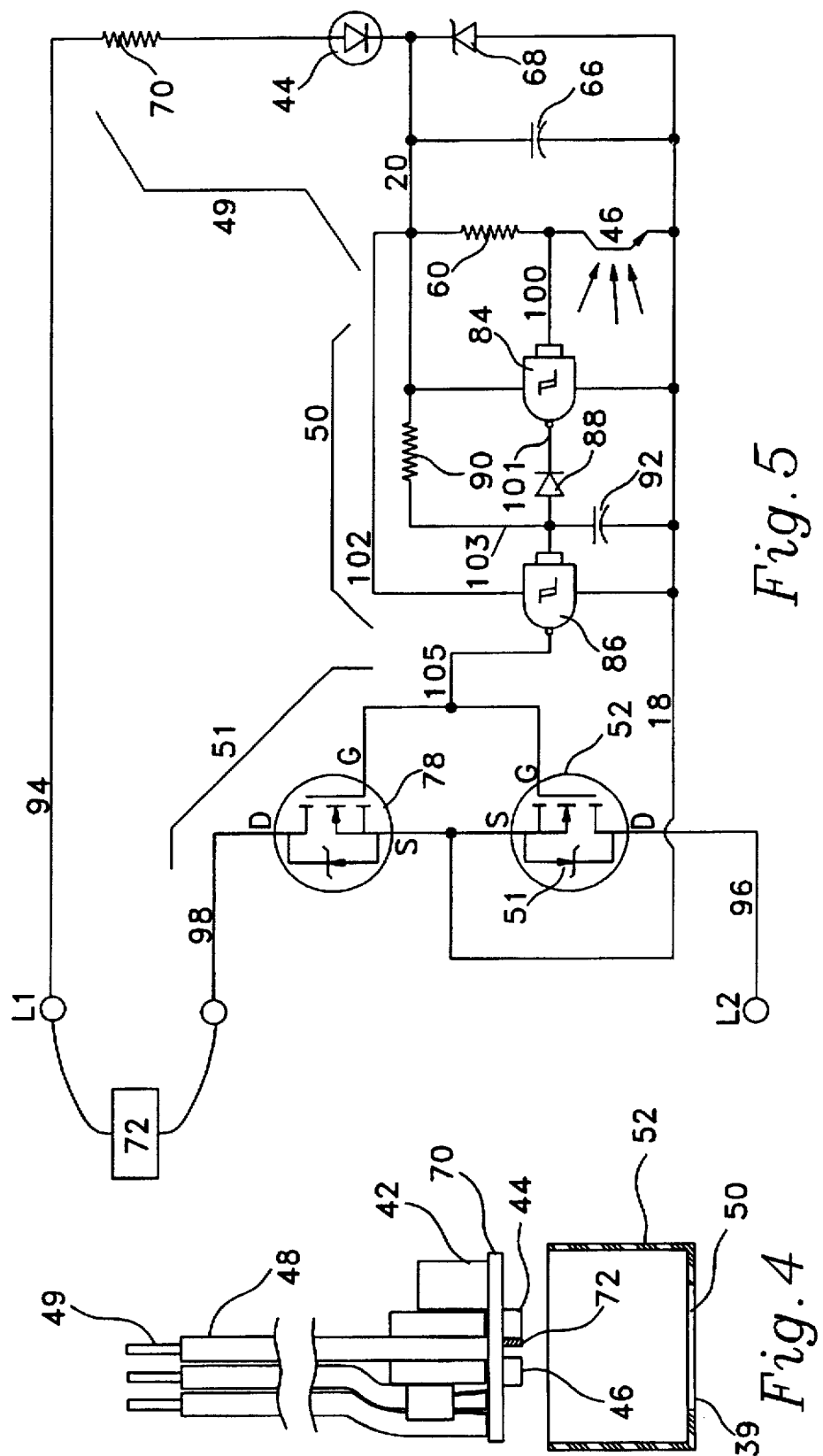

LOW OIL DETECTOR WITH AUTOMATIC RESET

BACKGROUND

1. Field of the Invention

The invention is directed toward optical sensors that differentiate between the presence of liquid and vapor. The invention is further directed toward such sensors that are designed to be applied to refrigeration compressors to protect them against extended operation under conditions of inadequate oil. The invention is further related to such oil sensors that incorporate a time delay between the time inadequate oil is detected and the time the compressor is stopped. The invention is further directed toward such oil sensors that further include means for periodically testing whether the oil supply has been reestablished and for restarting the compressor on such a condition.

2. Discussion of Similar Art

My U.S. Pat. No. 5,278,426 discloses a device for monitoring liquid level within a pressurized system. The optical portion of the device disclosed by the patent as well as the mechanical packaging is substantially the same as that disclosed herein. Barbier 426 discloses no control arrangement as is disclosed and claimed in the present invention.

OPERATION AND DISADVANTAGES OF PRIOR SYSTEMS

Lubrication failure sensors also known as "oil safety switches" are well known in the refrigeration industry and in the arts employing engines and mechanical compressors. Most refrigeration compressors and engines manufactured heretofore employed an oil pump to withdraw oil via a pickup tube from an oil reservoir or crankcase and supply it under pressure in the range of 10 to 50 psig to the various bearings, journals and pistons requiring lubrication. When a lubrication failure occurred, either because of pump failure or because of drop in the oil level below the pickup tube inlet experience taught that it was essential to stop the compressor within 60 to 90 seconds or compressor damage would occur. To protect the compressor against such an occurrence devices called oil-safety switches were developed. Generally these employed a differential pressure sensor to compare oil pump outlet pressure with oil pump inlet or reservoir pressure to sense a drop in oil pressure. On a drop below a predetermined minimum, a first switch started a timer having a preset period in the range of 10 to 90 seconds. On elapse of the preset time, a second switch, actuated by the timer, opened a circuit to the compressor controller, thereby stopping the compressor. If during the timing period, the oil pressure was restored, the timer reset without stopping the compressor. If the oil pressure dropped thereafter, the timer provided the full preset timing period.

One common type of oil safety switch employed bellows having one side connected by a capillary tube to the oil pump discharge and the other side connected by a capillary tube to the oil pump inlet or to the crankcase. When the oil pressure differential dropped below a preset value, a first switch applied electric heat to a bimetal. After a period, typically 60 to 90 seconds, the bimetal would latch open a switch controlling the compressor, stopping it until the switch was manually reset.

Once the oil safety switch 'timed out' and stopped the operation of the compressor, it would not restart without manual. intervention because a mechanical or electrical 'lock-out' was provided that required a button to be pressed to restart. No automatic 'remonitoring' of the oil level was possible without restarting the compressor to observe whether there was or was not oil pressure. Such an exploratory restart would have been hazardous for the compressor since oil level or pump performance might not have been restored and the compressor might have been repeatedly restarted in an effort to sense restoration of oil. level when there was no oil at all. Further, the capillary tubes used to connect the bellows to the system frequently broke and allowed the CFC refrigerant, where used, to escape to harm the stratospheric ozone. Further, such a pressure differential type oil-safety switch could not be employed on the many compressors manufactured without oil pumps.

There are many possible scenarios or environments within which a refrigeration system may temporarily exhibit a low oil level. Yet with proper monitoring, such systems might be safely restarted without any other intervention, such as adding more oil or making some physical change or repair to the system. The oil level and oil safety devices now known to me do not offer, and the literature and art do not suggest or teach, mechanisms of processes for achieving such objectives.

OBJECTS AND ADVANTAGES OF PRESENT INVENTION

Therefore, it is a primary objective of the present invention to provide an oil sensing system which employs optical means to detect presence of and lack of oil.

It is further objective of the invention to provide an oil sensing system which is not prone to leaking CFC refrigerants or lubricant to the atmosphere.

It is a further objective to provide a such an oil sensing system sensor which, on sensing a low oil level, provides a time delay before stopping the compressor.

It is a further objective to provide an oil sensing system which, after having stopped a compressor on sensing low oil level, checks to determine if the oil level has been re-established and, if so, only then restarts the compressor.

It is a further objective to provide such an oil sensing system with a time delay where the time period resets to its original value whenever a high oil level is detected.

It is a further objecting to provide a system which provides means for manually restarting the compressor, even in the absence of oil at the sensor.

It is a further objective to provide such a system employing a novel low power, high efficiency switching circuit.

It is a further objective to provide an oil level sensing system which does not depend on the presence of an oil pump to function.

It is a further objective to provide such a system which can be fully contained within a hermetic compressor.

SUMMARY OF THE INVENTION

An oil loss protection system including an oil loss sensing module, for a motor driven refrigeration compressor having an oil containing reservoir. The reservoir includes a wall. The wall has an oil side and an outside. The oil within the reservoir has a higher and a lower oil level. The motor is controlled by the oil loss sensing system. The oil loss sensing module comprises fitting means for positioning in operative relation to the oil level, circuit means for controlling the motor and optical means for interfacing and interacting with the oil level.

The optical means includes window means sealed to the fitting means. The window means has an oil side and a circuit side. The window means has a prismatic surface positioned on the oil side and subject to the oil level and a substantially planar surface positioned on the circuit means side.

The circuit means comprises an encapsulated electronic circuit positioned substantially adjacent the planar surface of the window means, the circuit comprises a power supply, a light source positioned to transmit light to the planar surface of the window means, a light sensor positioned to receive light from the planar surface of the window means and to respond to a lower and a higher oil level. The circuit means also includes alternating current switch means for starting and stopping the motor means The circuit further includes resettable timing means responsive to the light sensor for opening the switch means and thereby stopping the compressor motor on the elapse of a predetermined time period after the sensor has responded to a lower oil level. Further, there are means responsive to the light sensor for resetting the timing means and for closing the switch means, thereby starting the compressor motor on a condition of higher oil level, whenever the higher oil level occurs after the timing means has responded to a condition of lower oil level and caused the switch means to open.

BRIEF DESCRIPTION OF THE DRAWINGS

The foregoing summary as well as the following description of preferred embodiments of the invention, will be better understood when read in conjunction with the appended drawings. For the purpose of illustrating the invention there are shown in the drawings embodiments which are presently preferred, it being understood, however, that the invention is not limited to the specific instrumentalities or the precise arrangement of elements disclosed.

FIG. 4 is an exploded view of the electronics module.

FIG. 5 is a schematic wiring diagram of the electronics module.

DETAILED DESCRIPTION OF THE INVENTION

Figure 1:
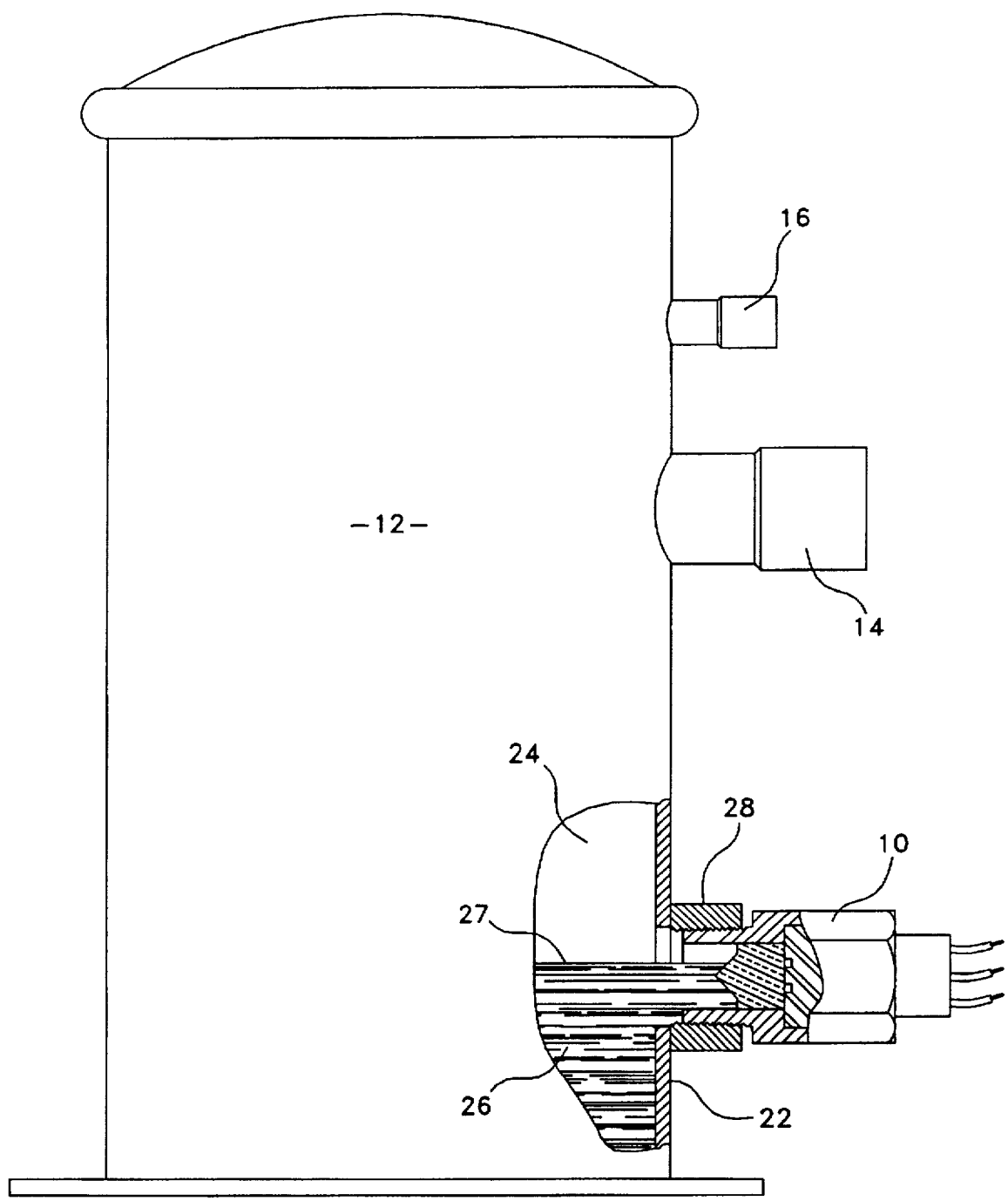
FIG. 1 is a side elevation in partial cross-section showing the sensor system of the invention installed in a compressor side wall.

Referring now to the drawings wherein like references are used to indicate like elements, there is shown in FIG. 1 a side view of compressor shell 12 having wall 22 and having suction inlet connection 14 and discharge outlet connection 16, within compressor shell 12 is mounted an electric motor 74, not shown, (see FIG. 6) and a compressor, also not shown. The compressor is direct connected to the motor. The compressor inside the shell 12 has flexible tubes, not shown, which connect to the suction 14 and discharge 16 connections. Low oil sensor system 10 is screwed into compressor fitting 28. Fitting 28 is positioned by the compressor manufacturer at a height which represents the minimum allowable oil level within the oil reservoir defined by compressor shell 22. Within the reservoir is a body of oil 26 and a body of vapor 24 laying above the oil with the interface 27 between vapor and oil being the oil level.

Figure 2:
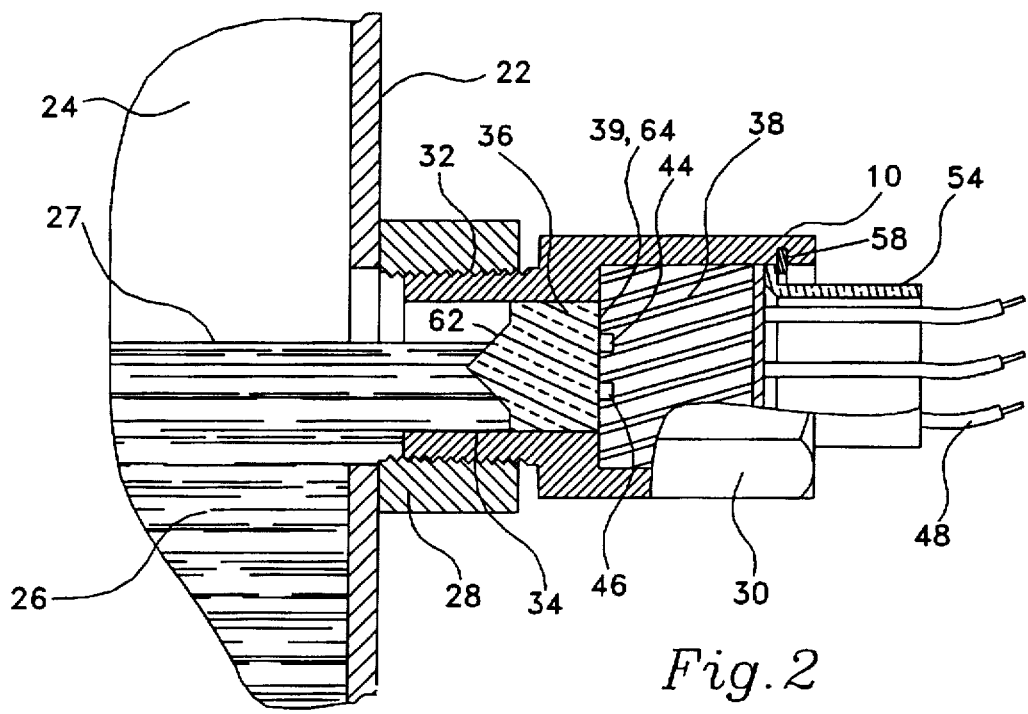
FIG. 2 illustrates, by a sectional view, the construction of the fitting which contains the sensor window and the electronics.

FIG. 2 is an enlarged detailed cross-sectional view of the low-oil sensor system 10 showing more clearly the threaded housing 30 for the sensor assembly sealed within the housing 30 is window 36 which provide light communication through the compressor wall. The window 36 has prismatic face 62 positioned on the oil side and planar face 64 facing the outside. A light source 44 and a light sensor 46 are both positioned adjacent face 64 of window 36. The light source 44 and the light sensor 46 are both embedded in electronic module 38 and positioned in and optically exposed to the module exterior at module face 39. A thimble 54 is secured by lock-ring 58 which is seated in groove 59. During the period that the oil level 27 is higher, that is covering more of the prismatic face 62 of prism 36, most of the light emitted by the source 44 is not reflected by the prismatic face 62 but instead traverses the prismatic interface 62, and is absorbed into and dissipated within the pool of oil 26. Therefore, during the higher oil period, light of low intensity is reflected back to the sensor 46 by reflection at the prismatic interface 62. By contrast, during periods when the oil level, is lower, that is, covering less of the prismatic face 62, and more of the prismatic face 62 is immersed in the vapor 24 residing over the oil pool 26, more of the light emitted by light 44 does not enter the pool of oil 26, but instead is internally reflected by prismatic face 62 and returns with higher intensity to the light sensor 46. It should be understood that the oil level may not have to fully cover or fully uncover prismatic face 62 for the circuit to operate as described.

Figure 3:
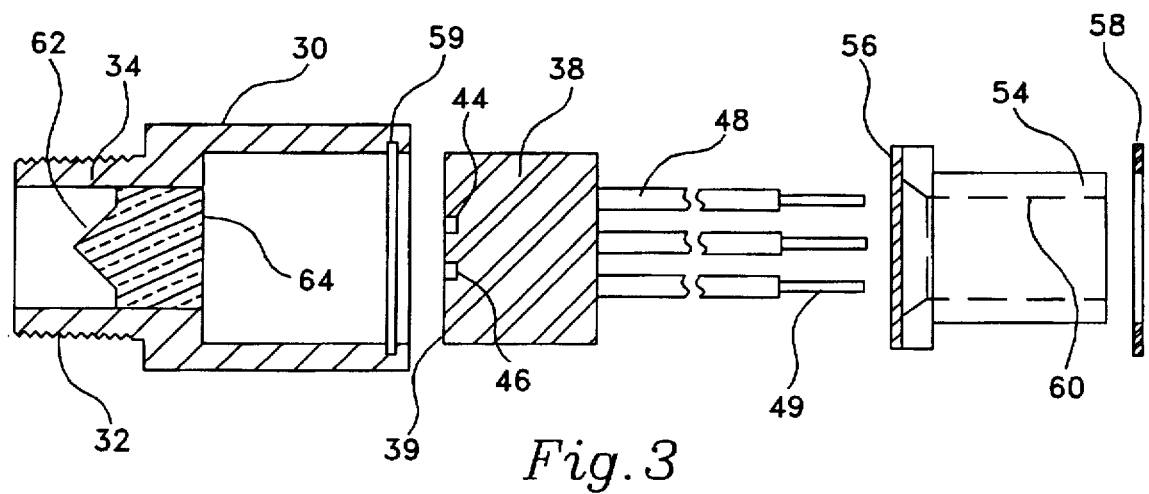
FIG. 3 shows an exploded view of the sensor fitting and the electronics module.

FIG. 3 shows, in an exploded view of the low-oil sensor assembly, the sensor housing 30 having threaded end 32, electronics module 38 having leads 48 with wires 49, thimble 54 and lock ring 58, all positioned as shown in FIG. 2. There is provided resilient member 56 for the purpose of ensuring positive pressure between the face 39 of the electronic module 38 and the planar face 64 of the window 36. Window 36 is sealed into bore 34 of fitting 30 by glass-steel soldering. Alternate sealing methods include epoxy cements or gaskets such as O-rings. In an alternate embodiment of the invention, both the fitting 30 and window 36 are molded in a single piece of a material transparent to the wavelengths of light emitted by the light source 44. Among such materials are epoxies and polystyrenes.

FIG. 4 illustrates the electronic sub-assembly 42 just prior to insertion into and encapsulation in shell 52 of module 38. Module shell 52 has an opening 50 at the bottom to allow the light source 44 and the light sensor 46 to have optical access to the planar face 64 of the window 36 via the face 39 of the of the electronic module 38. After the electronics sub-assembly 42 is inserted into shell 52, a thermo-setting liquid potting compound, such as epoxy is poured into the shell 52, thereby covering, supporting, protecting and sealing the electronic components in sub-assembly 42 of the module 38. The electronic sub-assembly 42 is mounted on one side of substrate 70. Light source 44 and light sensor 46 are mounted on the other side of substrate 70 in a position where they can emit and receive light through opening 50 of shell 52. Opaque barrier 72 is provided between the light source and the sensor to prevent light from the source from directly affecting the sensor.

In FIG. 5, displaying the schematic wiring diagram of the components in electronic sub-assembly 42 embedded within module 38, there are found leads 94, 96 and 98. These are generally identified in FIG. 3 as leads 48. Of these leads, 94 labeled L1, and 96 labeled L2, are the power supply from an ordinary high voltage alternating current source such as 11.5 volt, 60 Hertz or 230 volt, 60 Hertz. Lead 98 is the controlled lead or alternating current output which supplies or stops flow of alternating current to load 72.

Electronic Components:

Within FIG. 5 the electronic components have the following typical values. All of the components listed below are incorporated into the electronics module 38 of FIG. 3.

| ITEM | Value | ITEM | Description |
| --- | --- | --- | --- |
| Resistors: | | Assorted Components: | |
| 70 | 48.7 kohm | 44 | Light Emitting Diode MLED71 |
| 60 | 274 kohm | 68 | 12 Volt Zener diode |
| 90 | 10 Megohm | 46 | Light detector MRD711 |
| Capacitors: | | 84, 86 | 4093 NAND gates |
| 66 | 6.8 uf | 88 | Diode |
| 92 | 22 uf | 52, 78 | MOSFET Power transistors FET1B IRFU320–400 v |

Other values may be selected depending on the desires and objectives of the designer.

Electronic Functional groups:

There are four discrete electronic functions operatively arranged in FIG. 5.

The AC switch group 51 is comprised of MOSFET 52 and MOSFET 78. These two MOSFETs are connected in series between L2, load 72 and L1. The drain (D) connection of MOSFET 78 is connected to one side of load 72 via line 98, and the drain (D) connection of MOSFET 52 is connected to L2 via line 96. The source (S) connections of the two MOSFETs are connected together and commoned with zero potential line 18 and the negative side of zener diode 68. The AC switch group 51 directly controls flow of alternating correct power to load 72 as explained below.

The oil level detection group 49 is comprised of load resistor 70, LED 44, Zener 68, capacitor 66 light detector 46 and resistor 60. The LED 44, Zener 68 and capacitor 66 also provide a regulated, filtered DC power supply for the remainder of the sensor system.

The time delay group 50 comprises the two NAND gates 84 and 86, capacitor 92 and diode 88 and resistor 90. NAND gates 84 has input 100 and output 101. NAND gate 86 has input 103 and output 105. Both NAND gates are connected to DC high voltage source 20 and common zero potential line 18. When the input voltage of a NAND gate is high, its output voltage is low. When input voltage of a NAND gate is low, its output voltage is high.

Circuit Operation:

DC Power Supply:

AC line voltage is supplied to line connections L1 and L2, the alternating current input. Load resistor 70 reduces the applied voltage to a value tolerable to LED 44. LED 44 both emits light, which is be transmitted through window 36 in behalf of the oil detection function and, in its diode capacity, provides half wave rectification of the applied AC voltage. Where the AC line voltage is in excess of the peak inverse capabilities of the LED, back-up diode 71 can be employed. Zener 68, which is connected across the oil level detection and time delay network, is rated for 12 volts and allows current flow to zero potential line 18 when the potential across it rises higher than its rating, thereby limiting the voltage to that value. Through its voltage limiting function, Zener 68 provides a modified square wave waveform. This square wave is filtered by capacitor 66 to a substantially regulated, filtered high voltage (12 v) DC output at conductor 20. This 12 volt DC output is employed as power supply by the remainder of the oil level detection group 49, the time delay group 50 and the MOSFET portion of the AC switch group 51.

Circuit Operation:

Oil Present at Sensor:

Light detector 46 has a lower resistance when exposed to light of greater intensity and a higher resistance when exposed to light of lower intensity. Light emitting diode (LED) 44 emits light only during the portion of the AC cycle when it is conductive. Its light output is therefore pulsating. When oil level 27 is high on or above prismatic surface 62, light emitted by LED 44 is transmitted into the body of oil 26 and is absorbed by the oil. Consequently light of relatively low intensity is reflected or otherwise returned to sensor 46. Therefore the resistance of sensor 46 is relatively high and the voltage at the input 100 of first NAND gate 84 is high, relative to the zero potential conductor 18. The high input voltage at input 100 of first stage NAND 84 establishes a low voltage at output 101 of NAND 84, thus providing a low voltage path from input 103 of second stage NAND 86 via diode 88. This drops the voltage at input 103 of second stage NAND gate 86 below its cutoff voltage, thereby driving the output voltage at 105 of NAND gate 86 above the four volt minimum required to hold the MOSFETs 52 and 78 in a conductive condition, thereby energizing alternating current output 98.

Paired MOSFETs as AC Switch

A typical MOSFET (metal-oxide semi-conductor field effect transistor) has three connections, a source (S), a drain (D) and a gate (G). When the drain is negative (having excess electrons) with respect to the source, electrons can flow from the drain to the source only when the gate is positive with respect to the source by a minimum potential of two to four volts called the cut-off voltage. By contrast, when the drain is positive to the source, electrons can flow freely through the MOSFET from the source to the drain regardless of the state of the grid voltage with respect to the source. This free flowing path, not controlled by gate (G), is provided by a diode 51 which is internal of the MOSFET construction.

When two MOSFET 52 and 78 are connected in series, with common source (S), no current can flow through the pair in either direction so long as the voltage between gate (G) and common sources (S) is below the cut-off voltage. This is because, though one of the two MOSFET's is always able to conduct in one direction, the other, in series with it, is always made non-conductive in that direction by the below-cut-off state of its grid voltage.

However, when a positive voltage which is much higher than the cut-off voltage is applied between grids (G) and sources (S) of the two MOSFETs, then whichever MOSFET previously prevented electron flow because of the state of its grid voltage, that MOSFET now allows electron flow. Therefore, with voltage between both gates (G) and commoned (S) above the cut-off voltage, The paired MOSFET's behave like a closed AC switch, thereby allowing full flow of alternating line current to and through load 72, via AC output 98.

The combined action of the two MOSFETs connected in this manner provides the equivalent of a low cost, low dissipation, physically small full-wave alternating current switch actuated by a very low power direct current control circuit.

The use of the two MOSFETs 52 and 78 in series as a full-wave alternating current switch provides the unusual advantages of extremely high efficiency leading to very low heat dissipation as well as low cost. The low heat dissipation allows high capacity alternating current switches of this design to be incorporated in compact potted or encapsulated circuits where excessive heat dissipation of any component would be destructive to the entire potted assembly.

Figure 6:
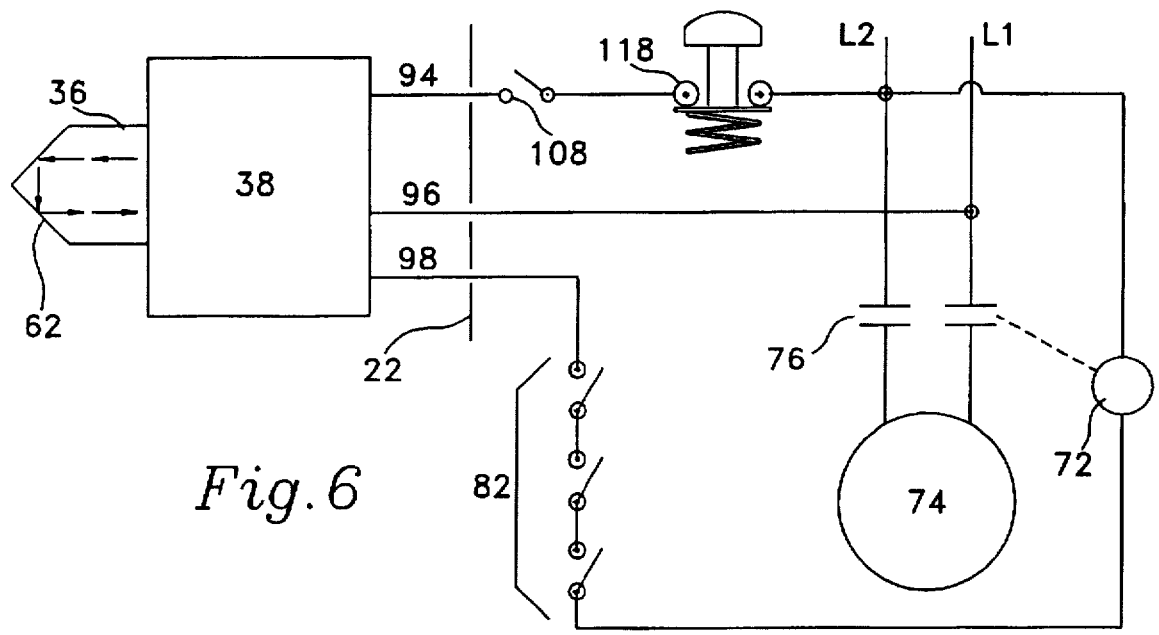
FIG. 6 is a schematic wiring diagram in which the sensor system is connected to the compressor control and power circuit further incorporating timers, counters and provisions for manual reset.

Oil Absent at Sensor:

When the oil level 27 falls lower on or below the prismatic surface 62, the surface 62 is immersed in vapor 24. The difference in refractive index between window 36 and vapor 24 causes the pulsating light emitted by LED 44 to be substantially fully reflected back to light detector 46 through the process known a total internal reflection. The pulsating light reaching light detector 46 causes it to conduct in a pulsing manner corresponding to the half wave pulsing light emitted by the LED. The resistor 60 and detector 46 together act as a voltage divider. In this voltage divider the reduced resistance of the detector 46 under higher light conditions acts to lower the gate voltage at the input 100 of NAND gate 84, the input also of time delay circuit 50. When the voltage at conductor 100, the input to first time delay stage, NAND gate 84, drops, the voltage at the output 101 of first stage NAND gate 84 rises. This causes diode 88 to become non-conductive, thereby allowing capacitor 92 to charge up over time through resistor 90 until the input 103 of second stage NAND gate 86 rises to the trigger voltage of second stage NAND gate 86. On high input voltage, the output 105 of second stage NAND gate goes below the trigger voltage of MOSFETs 62 and 78, causing the MOSFETs to become non-conductive on the portion of the alternating cycle controlled by the MOSFET gate voltage and thereby stopping AC current flow to and through load Compressor Control:

Safety and Protective Devices:

In FIG. 6, load 72 is connected as the magnetic coil of a compressor controlling contactor having contacts 76. When load 72 is energized, contacts 76 close and compressor motor 74 operates. When load 72 is de-energized, contacts 76 open and compressor motor 74 stops. Switches 82 are primarily safety devices such as high pressure switches sensing the compressor discharge pressure and stopping the compressor when the pressure exceeds a preset value, low pressure switches sensing suction pressure of a refrigerating system, closing and starting the compressor on pressure rise and opening and stopping the compressor on fall in suction pressure. Other protective devices provided as switches 82 are discharge temperature thermostats and over-current devices.

Operating and Service Controls:

In FIG. 6, switches 108 and 118 have provided in the alternating current supply lead 94 to the electronic module 38. Switch 108 represents the operating control device for starting and stopping the compressor for temperature control. In one embodiment, switch 108 is a line thermostat sensing the temperature of the cooled space or product and starting and stopping the compressor to maintain the temperature of the cooled environment at the preset temperature.

Time Delay Logic:

When compressor 74 is started, oil level 27 may be low on or below the prism 62. A time delay period, described in connection with FIG. 5, is provided during which the compressor 74 is permitted to operate for a predetermined period after the low oil condition is detected. If during this initial period, the oil level 27 rises higher on or covers prismatic face 62, the timer is reset and the compressor is allowed to operate continuously until operation is terminated by the operating control 108 or limit controls 82. If, on the other hand, the oil level 27 does not rise sufficiently, during the initial time delay period, the compressor is stopped at the end of the time delay period by the timing circuit 50 acting on MOSFETs 52 and 78. Whenever switch 108 opens, stopping the compressor 74, the timer circuit 50 in FIG. 5, embedded in module 38 is caused to reset to its initial time value. Thereafter, when switch 108 closes to restart the compressor, the full time delay built into the time delay circuit 50 becomes operative.

Manual Restart Switch:

When service personnel attend equipment which has stopped, diagnostic operations are facilitated when convenient means are provided for determining which safety devices have caused the stoppage. In FIG. 6, normally closed switch 118 is provided in AC lead 94 of module 38. Since switch 118 is normally closed and is manual, its presence does not affect normal operation of the system or the module 38 at all. However, when a service-person arrives on the job, having been called because of a complaint of system non-operation, she can restart the system and enable it to run for the time-delay period simply by pressing and releasing manual switch 118. When switch 118 is depressed, it removes power from module 38. This causes the timing circuit 50, within the module, to reset. When manual switch 118 is released, power is reapplied to the circuit 50 within module 38 thereby activating the circuit to energize load 72 and start compressor 74 even though oil level 27 is below prismatic surface 62. The compressor is allowed to run, at least for the duration of the time delay preset within circuit 50, or until the compressor is stopped by another control or safety 82. A competent service person will have installed her gages and meters prior to pressing manual switch 118. This will allow her to quickly make and record the necessary observations of pressure, temperature, current etc. for effective diagnosis of the system problem. Of course, if oil level 27 rises sufficiently to cover prismatic surface 62 during the time delay period and no protective device 82 operates, the compressor will continue to run until stopped by operating control 108.

Figure 7:
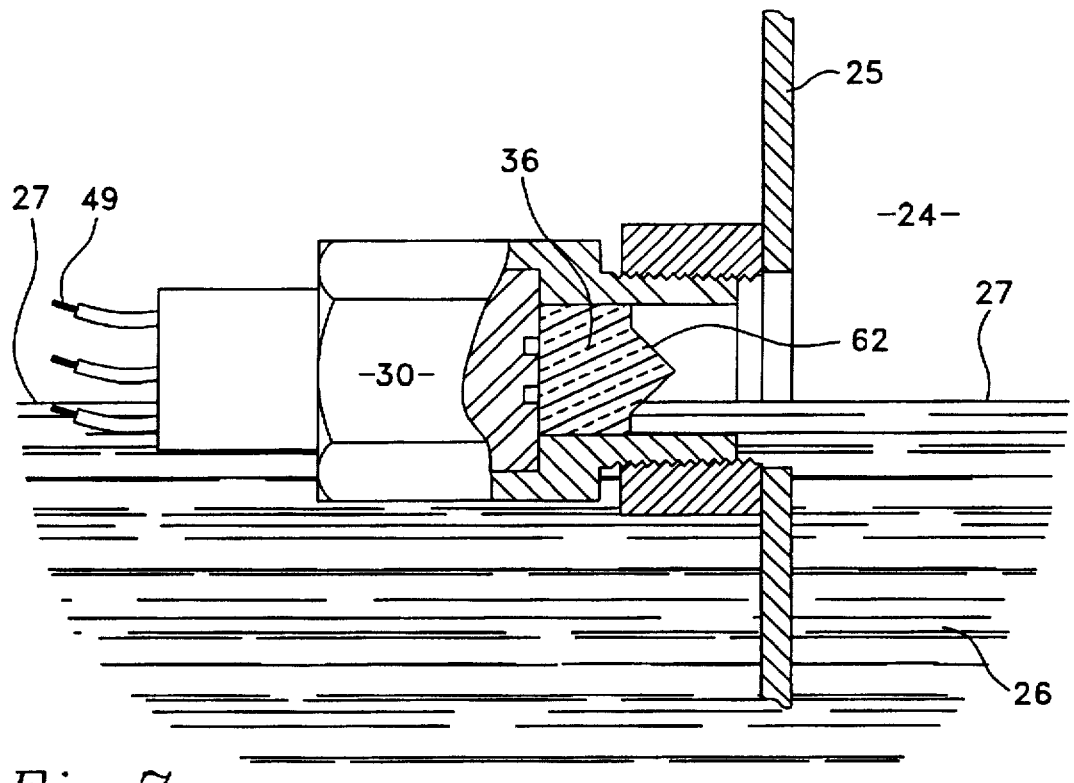
FIG. 7 is a side elevation of the sensor system positioned fully within the compressor oil reservoir.

FIG. 7 shows the oil sensing module 30 installed fully within a compressor 12 and mounted to interior support 25. The module 30 is positioned so oil level 27 normally covers or is higher on prismatic surface 62. When oil level 27 drops to a position lower on or below prismatic surface 62, the compressor is stopped after the time delay preset in circuit 50. The installation of module 30 fully within the compressor 12 allows elimination of fitting 28 thereby reducing propensity for leaks and reducing cost. In one embodiment of the invention, wires 94, 96 and 98 are routed through wall 22 of compressor 12 to an external control circuit. In another embodiment of the invention the MOSFETs are used to directly control the compressor.

From the foregoing description, it can be seen that the present invention comprises an improved device especially adapted for sensing low oil level in a machine or refrigeration compressor, and especially in such a machine riot equipped with an oil pump. It will be appreciated by those skilled in the art that changes could be made to the embodiments described in the foregoing description without departing from the broad inventive concept thereof. It is understood, therefore, that this invention is not limited to the particular embodiment or ?embodiments disclosed, bit is intended to cover all modifications which are within the scope and spirit of the invention as defined by the appended claims.

I claim:

1. An oil loss protection system for use with an alternating current supply, the system including an oil loss sensing module for a refrigeration compressor having an oil containing reservoir, the reservoir including a wall, the wall having an oil side and an outside, the oil within the reservoir having a higher and a lower oil level, actuating means, controlled by the oil loss sensing module, for starting and stopping the compressor, the oil loss sensing module comprising:

a) a fitting positioned in operative relation to the oil level, b) optical means for interfacing and interacting with the oil level, the optical means comprising:
window means sealed to the fitting, the window means having an oil side and a circuit side, the window means having a prismatic surface positioned on the oil side and subject to the oil level and a substantially planar surface positioned on the circuit side, c) encapsulated electronic circuit means having an alternating current supply and an alternating current output, the encapsulated circuit means positioned substantially adjacent the planar surface of the window means, the circuit means comprising:
rectifying means for supplying direct current to the circuit means,
a light source positioned to transmit light to the planar surface of the window means,
a light sensor positioned to receive light from the planar surface of the window means and to respond to a lower and a higher oil level,
alternating current switch means for controlling the alternating current output and thereby starting and stopping the compressor actuating means,
resettable timing means responsive to the light sensor for opening the switch means and thereby stopping the compressor actuating means on the elapse of a predetermined time period after the sensor has responded to a lower oil level, and
means responsive to the light sensor for resetting the timing means and for closing the alternating current switch means, thereby starting the compressor actuating means, on a condition of higher oil level occurring after the timing means has responded to a condition of lower oil level and caused the switch means to open.

2. An oil loss protection system as recited in claim 1, where the light source is the rectifying means.

3. An oil loss protection system as recited in claim 2 where the alternating current switch means comprises at least two metal-oxide-semi-conductor-field-effect-transistors (MOSFETs).

4. An oil loss protection system as recited in claim 3 further providing that each MOSFET includes connections identified as Source, Drain and Gate, and further providing that two MOSFET's are connected Source to Source between the actuating means and the alternating current supply.

5. An oil loss protection system as recited in claim 4 further providing that the circuit means includes a common connection and the joined Source connections of the MOSFETs are connected to said common connection.

6. An oil loss protection system as recited in claim 5 further including switch means external to the encapsulated circuit means, said switch means being positioned in the alternating current supply for temporarily interrupting power to the circuit means, whereby the timing means is reset and the actuating means re-energized for the duration preset by the timing means.

7. An oil loss protection system as recited in claim 6 where the oil sensing module is positioned within the reservoir.

8. An oil loss protection system as recited in claim 6 where the oil sensing module is positioned in the reservoir wall with the circuit side on the outside.

9. An oil loss protection system as recited in claim 6 where the external switch means is a manually actuated normally closed switch.

10. An oil loss protection system as recited in claim 6 where the external switch means is a temperature control thermostat.

* * * * *